(12) United States Patent
Kankan et al.

(10) Patent No.: US 9,012,689 B2
(45) Date of Patent: Apr. 21, 2015

(54) PROCESS FOR THE PREPARATION OF O-DESMETHYL VENLAFAXINE AND INTERMEDIATE FOR USE THEREIN

(75) Inventors: Rajendra Narayanrao Kankan, Maharashtra (IN); Dharmaraj Ramachandra Rao, Maharashtra (IN); Manohar Raghunath Surve, Maharashtra (IN)

(73) Assignee: Cipla Limited, Mumbai (IN)

( * ) Notice: Subject to any disclaimer, the term of this patent is extended or adjusted under 35 U.S.C. 154(b) by 578 days.

(21) Appl. No.: 13/381,870

(22) PCT Filed: Jul. 14, 2010

(86) PCT No.: PCT/GB2010/001341
§ 371 (c)(1),
(2), (4) Date: Mar. 8, 2012

(87) PCT Pub. No.: WO2011/007136
PCT Pub. Date: Jan. 20, 2011

(65) Prior Publication Data
US 2012/0157544 A1    Jun. 21, 2012

(30) Foreign Application Priority Data
Jul. 16, 2009 (IN) .......................... 1651/MUM/2009

(51) Int. Cl.
*C07C 211/00* (2006.01)
*C07C 229/34* (2006.01)
*A61K 31/24* (2006.01)
*C07C 215/64* (2006.01)

(52) U.S. Cl.
CPC ............... *C07C 229/34* (2013.01); *A61K 31/24* (2013.01); *C07C 215/64* (2013.01); *C07C 2101/14* (2013.01)

(58) Field of Classification Search
CPC ... A61K 31/135; A61K 31/19; A61K 31/205; C07C 2101/14; C07C 215/54
USPC .................. 514/554, 574, 654; 564/336, 374; 562/590
See application file for complete search history.

(56) References Cited

U.S. PATENT DOCUMENTS

| 4,535,186 A | 8/1985 | Husbands et al. |
|---|---|---|
| 6,673,838 B2 * | 1/2004 | Hadfield et al. .............. 514/554 |
| 6,689,912 B2 | 2/2004 | Weber |
| 7,491,848 B2 | 2/2009 | Pospisilik et al. |
| 2010/0286447 A1 * | 11/2010 | Tyagi et al. ................... 564/356 |

FOREIGN PATENT DOCUMENTS

| EP | 1213279 A1 | 6/2002 |
|---|---|---|
| WO | 0059851 | 10/2000 |
| WO | 02064543 A2 | 8/2002 |
| WO | 2008093142 A1 | 8/2008 |
| WO | 2009084038 A2 | 7/2009 |
| WO | 2011007136 A2 | 1/2011 |
| WO | 2011007136 A3 | 1/2011 |

OTHER PUBLICATIONS

Chavan, Subhash P., Practical synthesis of (±)—venlafaxine, Synthetic Communications, XP008089921, 2007, 3901-3906, vol. 37, Taylor & Francis Group, LLC.
Davies, Huw M. L., Enantioselective synthesis of β-Amino esters and its application to the synthesis of the enantiomers of the antidepressant venlafaxine, Chem. Commun., XP-002644687, 2006, pp. 3110-3112, The Royal Society of Chemistry 2006.
Foreign communication from a priority application—International preliminary report on patentability, PCT/GB2010/001341, Jan. 17, 2012, 8 pages.
Foreign communication from a priority application—International search report and written opinion, PCT/GB2010/001341, Jul. 12, 2011, 11 pages.

* cited by examiner

*Primary Examiner* — Sudhakar Katakam
(74) *Attorney, Agent, or Firm* — Conley Rose, P.C.; Rodney B. Carroll

(57) ABSTRACT

The present invention relates to a compound of formula A, wherein R is alkyl.

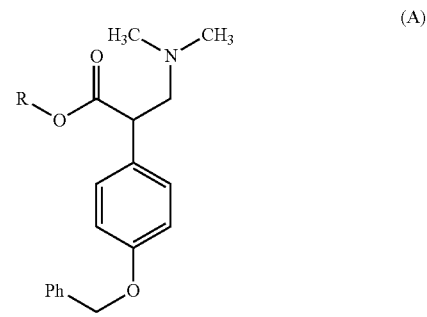

(A)

Compound A may be used as an intermediate in the preparation of O-desmethyl venlafaxine or a salt thereof, and the present invention provides such a preparation, as well as a process for preparing the compound of formula A.

29 Claims, No Drawings

PROCESS FOR THE PREPARATION OF O-DESMETHYL VENLAFAXINE AND INTERMEDIATE FOR USE THEREIN

CROSS-REFERENCE TO RELATED APPLICATIONS

This application is a filing under 35 U.S.C. 371 of International Application No. PCT/GB2010/001341 filed Jul. 14, 2010, entitled "Process for the Preparation of O-Desmethyl Venlafaxine and Intermediate for Use Therein," claiming priority of Indian Patent Application No. 1651/MUM/2009 filed Jul. 16 2009, which applications are incorporated by reference herein in their entirety.

FIELD OF THE INVENTION

The present invention relates to a process for the preparation of O-desmethyl venlafaxine (ODV) and pharmaceutically acceptable salts thereof.

In particular, the invention relates to a novel key intermediate useful in the synthesis of O-desmethyl venlafaxine (ODV) and process for its preparation.

BACKGROUND

O-Desmethyl Venlafaxine (ODV), chemically known as 4-[2-dimethylamino-1-(1-hydroxy-cyclohexyl)-ethyl]-phenol is a major metabolite of venlafaxine. It is represented by the structural formula V as shown below.

V

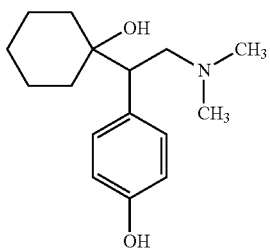

In vivo studies suggest that ODV is a more potent inhibitor of nor-epinephrine and serotonin uptake than venlafaxine. An imbalance among neurotransmitters is the cause of depression. Serotonin and norepinephrine are two neurotransmitters released by nerves in the brain. Desvenlafaxine works by preventing the reuptake of serotonin and epinephrine by nerves after they have been released. Since uptake is an important mechanism for removing released neurotransmitters and terminating their actions on adjacent nerves, the reduced uptake caused by desvenlafaxine increases the effect of serotonin and norepinephrine in the brain, which helps to maintain mental balance and thus desvenlafaxine is mainly useful to control depression.

Venlafaxine and ODV were first claimed and processes for their preparation were disclosed in U.S. Pat. No. 4,535,186. The process is represented as shown below in the Scheme 1.

SCHEME 1

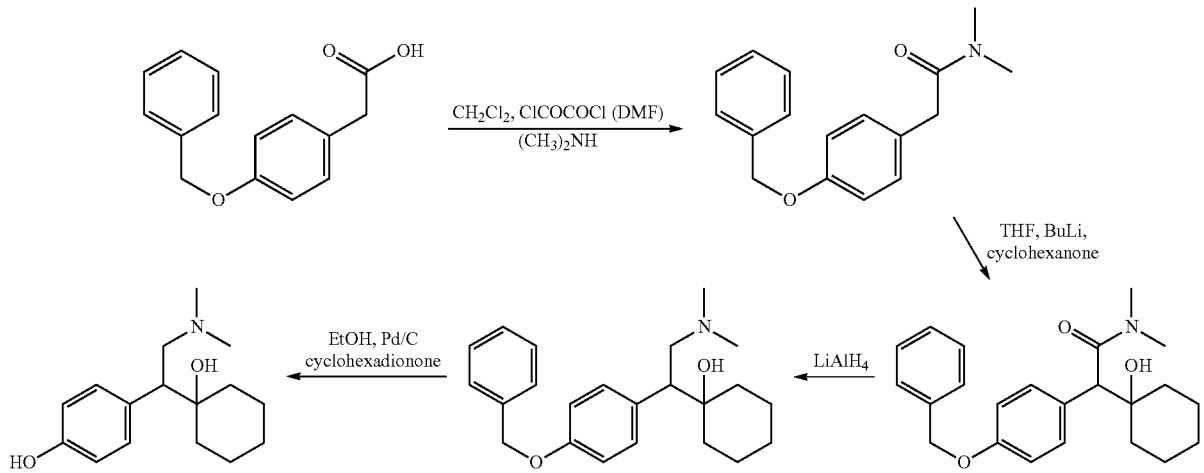

The process involves debenzylation of benzylated venlafaxine by catalytic hydrogenation. However, preparation of benzylated venlafaxine involves in situ generation of aluminium hydride, by reacting lithium aluminium hydride with concentrated sulphuric acid. Handling these reagents on a plant scale is very difficult and hazardous.

WO2000/059851, WO2002/064543, U.S. Pat. No. 6,689,912, and US2007/0299283 provide alternative processes for preparing ODV, which proceed via the demethylation of venlafaxine. However, these reactions involve, respectively: the use of demethylating agents such as diphenyl phosphine and n-butyllithium; an alkali metal salt of trialkylborohydride; high molecular weight alkane or arene thiolate anions in high boiling point solvents such as PEG-400; and metal sulfides such as sodium sulfide in a solvent 1-methylpyrrolidone. These reagents are expensive, toxic and/or hazardous and require extensive purification procedures to isolate the desvenlafaxine and/or corresponding by-products. The processes give moderate to low yields and impure end products and thus are unsuitable for industrial implementation.

WO2008/093142 discloses a preparation of ODV, which involves debenzylation of 1-[1-(4-benzyloxy-phenyl)-2-dimethylamino-ethyl]-cyclohexanol. However, the preparation of amidocyclohexanol involves the use of strong, non-nucleophilic bulky and sterically hindered bases such as lithium hexamethyl disilazide.

WO2009/084038 discloses a process for the preparation of O-desmethyl-venlafaxine, and pharmaceutically acceptable salts thereof by demethylating venlafaxine or salts using an alkali or alkaline earth metal salt of a mercapto acid or its derivative, such as mercapto alcohols, heterocyclic mercaptans, xanthates, thioacids or mixtures thereof in the presence of an organic solvent.

Thus, there exists a need for an improved process for the preparation of ODV or its pharmaceutically acceptable salts which is safe, short, economical, high yielding, and environmentally friendly, and which avoids the use of potentially hazardous reagents.

OBJECTS OF THE INVENTION

The object of the present invention is to provide an improved process for preparing ODV and pharmaceutically acceptable salts thereof.

Another object is to provide an improved intermediate that is suitable for use in the preparation of ODV.

Yet another object of the present invention is to provide a process which is simple, economical and suitable for industrial scale-up.

SUMMARY OF THE INVENTION

According to a first aspect of the present invention, there is provided a compound of formula A

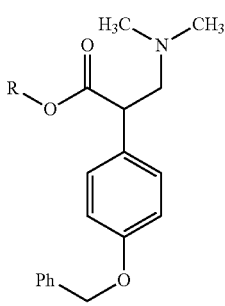

(A)

wherein R is an alkyl group. Compound A is a 2-(4-benzyloxy-phenyl)-3-dimethylamino-propionic acid alkyl ester. Preferably, R is a C1-10 alkyl group. The alkyl group may be straight- or branched-chain. For example, R may be methyl, ethyl, propyl such as i-propyl or n-propyl, butyl such as n-butyl, pentyl or hexyl. More preferably, R is a C1-C3 alkyl group. Most preferably, R is methyl or ethyl.

According to another aspect of the present invention, there is provided a process for preparing a compound of formula A as defined above

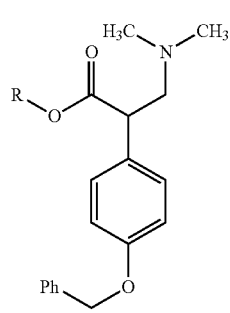

(A)

wherein R is an alkyl group, the process comprising:

a) esterifying (4-benzyloxy-phenyl)-acetic acid to form a (4-benzyloxy-phenyl)-acetic acid alkyl ester

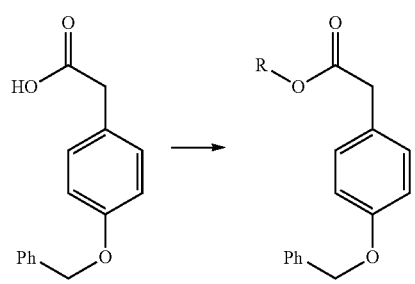

wherein R is as described above;

b) refluxing the (4-benzyloxy-phenyl)-acetic acid alkyl ester with paraformaldehyde typically in the presence of an inorganic base and a phase transfer catalyst to form a 2-(4-benzyloxy-phenyl)-acrylic acid alkyl ester;

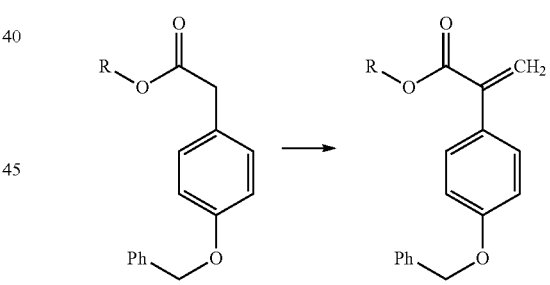

wherein R is as described above; and c) reacting the 2-(4-benzyloxy-phenyl)-acrylic acid alkyl ester with dimethyl amine typically in the presence of a Lewis acid catalyst to form compound A.

Preferably, R is a C1-10 alkyl group. The alkyl group may be straight- or branched-chain. For example, R may be methyl, ethyl, propyl such as i-propyl or n-propyl, butyl such as n-butyl, pentyl or hexyl. More preferably, R is a C1-C3 alkyl group. Most preferably, R is methyl or ethyl.

In an embodiment, esterification comprises reacting the acid of formula I with an alcoholic acid solution.

In an embodiment, the esterification comprises reacting (4-benzyloxy-phenyl)-acetic acid with a mixture of an alcohol and thionyl chloride or potassium carbonate and dimethyl sulfate. The alcohol may have the formula R'—OH, wherein R' is an alkyl group. Preferably, R' is a C1-C3 alkyl group. More preferably, R' is methyl or ethyl. Most preferably, the alcohol is methanol.

In an embodiment, an inorganic base used in step b). The base may be selected from: an alkali metal hydroxide, preferably sodium hydroxide or potassium hydroxide; and an alkali metal carbonate, preferably potassium carbonate, sodium carbonate or cesium carbonate. Preferably, the inorganic base is an alkali metal carbonate, more preferably potassium carbonate.

In an embodiment, a phase transfer catalyst is used in step b). The catalyst may be selected from: tetrabutyl ammonium hydrogen sulfate; an ammonium halide, preferably triethyl benzyl ammonium chloride; an alkyl ammonium halide, preferably tetrabutyl ammonium bromide or tetrabutyl ammonium iodide, most preferably tetrabutyl ammonium iodide.

Step b) may be carried out in the presence of an organic solvent selected from toluene, chlorobenzene and o-xylene; preferably toluene.

In an embodiment, the source of dimethyl amine in step c) is dimethyl amine gas or an alcoholic solution of dimethyl amine. The alcohol may have the formula R'—OH, wherein R' is an alkyl group. Preferably, R' is a C1-C3 alkyl group. More preferably, R' is methyl or ethyl. Most preferably, the alcohol is methanol.

In an embodiment, a Lewis acid catalyst is used in step c). The Lewis acid catalyst may be selected from zinc chloride, ferric chloride, aluminium chloride, lithium perchlorate and stannic chloride; preferably from ferric chloride and lithium perchlorate.

Advantageously, steps b) and c) are carried out without isolation of the compound 2-(4-benzyloxy-phenyl)-acrylic acid alkyl ester.

The present invention provides a novel process for the preparation of ODV with improved yield, which is amenable to large scale production, as the reaction conditions can be easily controlled. The preparation of intermediate can be one pot and also offers a simple work-up procedure with improved yield and quality and with minimum contamination by process impurities.

According to another aspect of the present invention, there is provided a process for preparing ODV of formula

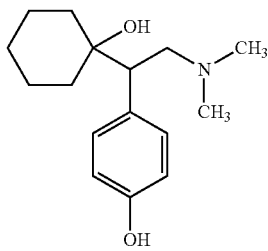 [SMILES: CN(C)CC(c1ccc(O)cc1)C1(O)CCCCC1]

comprising converting compound A as described above to ODV. In an embodiment, the compound A has been prepared by a process as described above.

In an embodiment, the conversion comprises reacting compound A with a Grignard reagent to form 1-[1-(4-benzyloxy-phenyl)-2-dimethylamino-ethyl]-cyclohexanol of formula

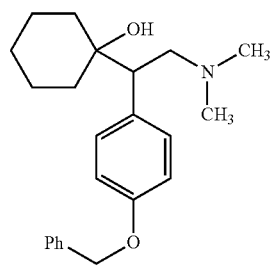 [SMILES: CN(C)CC(c1ccc(OCc2ccccc2)cc1)C1(O)CCCCC1]

followed by deprotection to obtain ODV.

The Grignard reagent is typically pentamethylene-1,5-bis (magnesium halide), i.e. $XMg-(CH_2)_5-MgX$, where X is halo, for example, chloro, bromo or iodo. The Grignard reagent may be prepared by refluxing activated magnesium turnings and iodine crystals with 1,5-dihalopentane in the presence of cyclic or acyclic ether. The dihalopentane may be selected from dibromopentane, dichloropentane and diiodopentane, preferably dibromopentane.

According to another aspect of the present invention, there is provided ODV prepared by a process described above.

The ODV so prepared may be formulated with one or more pharmaceutically acceptable excipients to provide a pharmaceutical composition. Such excipients and compositions are well known to those skilled in the art.

According to another aspect of the present invention, there is provided a pharmaceutical composition comprising ODV or an acid addition salt thereof as described above together with one or more pharmaceutically acceptable excipients.

According to yet another aspect of the present invention, there is provided ODV or an acid addition salt thereof as described above for use in medicine.

According to a still further aspect of the present invention, there is provided ODV or an acid addition salt thereof as described above for use in maintaining mental balance and thus mainly for use in controlling depression.

The invention is hereinafter detailed in greater details, no part of which may be construed as restrictive to the scope of the instant invention.

DETAILED DESCRIPTION OF THE INVENTION

In an embodiment of the present invention, there is provided a process for the preparation of novel intermediate 2-(4-benzyloxy-phenyl)-3-dimethylamino-propionic acid alkyl ester of formula A, which can be schematically represented as shown below in scheme 2.

SCHEME 2

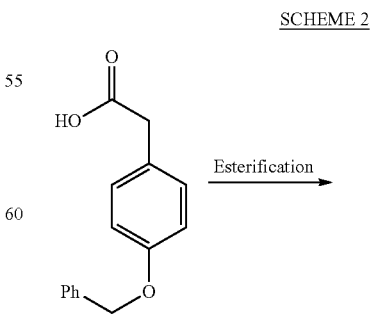

(4-Benzyloxy-phenyl) acetic acid

-continued

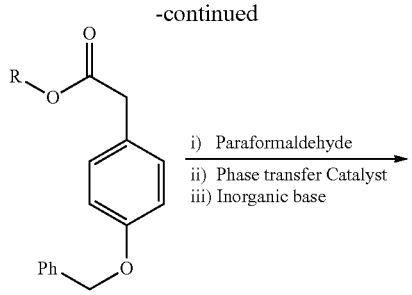

(4-Benzyloxy-phenyl)-
acetic acid alkyl ester

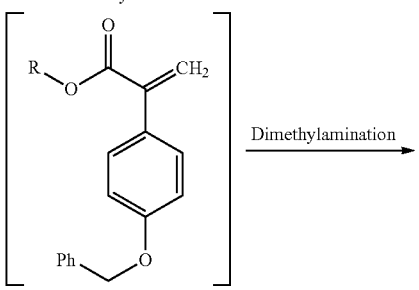

2-(4-Benzyloxy-phenyl)-
acrylic acid alkyl ester

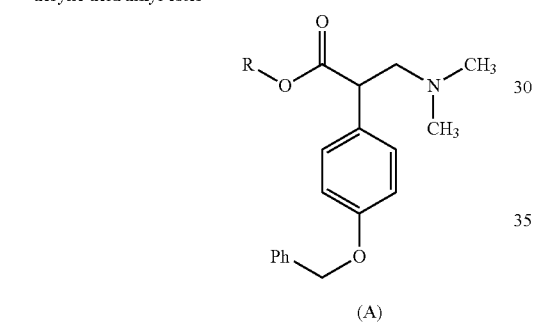

(A)

wherein R is an alkyl group, preferably a C1-C10 alkyl group, more preferably methyl or ethyl. [The bracket indicates an intermediate that may or may not be isolated, but is preferably not isolated in the integrated process.]

Accordingly, in an embodiment, the present invention provides a process for the preparation of novel intermediate 2-(4-benzyloxy-phenyl)-3-dimethylamino-propionic acid alkyl ester, of formula (A), comprising steps a), b) and c), as described below.

Step a): esterifying (4-benzyloxy-phenyl)acetic acid of the formula I

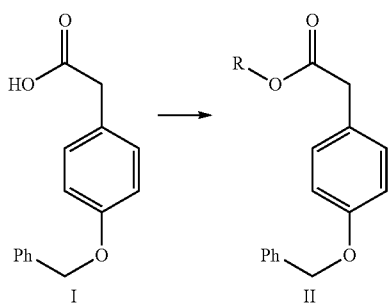

wherein R is as described above, in the presence of a suitable esterifying agent to form (4-benzyloxy-phenyl)-acetic acid alkyl ester of the formula II.

Typically, the esterification involves reacting the (4-benzyloxy-phenyl)acetic acid with an alcoholic acid solution. The acid may be hydrochloric acid or sulfuric acid and the alcohol may be methanol. Most particularly, esterification is carried out in a mixture of alcohol and thionyl chloride or potassium carbonate and dimethyl sulfate; preferably alcohol and thionyl chloride; most preferably methanol and thionyl chloride.

The esterification may be carried out at a temperature ranging from 0° C. to the reflux temperature of the selected solvent, preferably from 5° C. to the reflux temperature of the selected solvent or more preferably from 10° C. the reflux temperature of the selected solvent.

Step b): refluxing the (4-benzyloxy-phenyl)-acetic acid alkyl ester, with p-formaldehyde in the presence of a suitable inorganic base and a phase transfer catalyst to form 2-(4-benzyloxy-phenyl)-acrylic acid alkyl ester of formula III

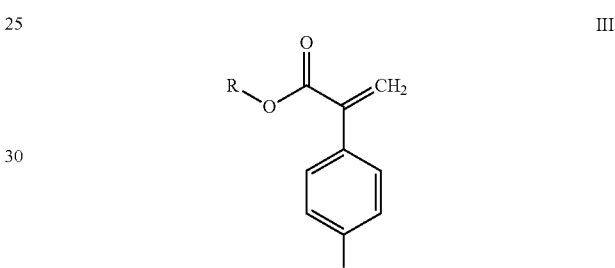

wherein R is as described above.

The inorganic base may be selected from alkali metal hydroxides such as sodium hydroxide, potassium hydroxide and alkali metal carbonates, preferably selected form potassium carbonate, sodium carbonate and cesium carbonate; most preferably potassium carbonate.

The phase transfer catalyst may be selected from: tetrabutyl ammonium hydrogen sulfate; ammonium halides such as triethyl benzyl ammonium chloride; alkyl ammonium halide such as tetrabutyl ammonium bromide or tetrabutyl ammonium iodide, most preferably tetrabutyl ammonium iodide.

The reaction may be carried out in the presence of an organic solvent. The solvent may be a high boiling organic solvent selected from toluene, chlorobenzene and o-xylene; most preferably toluene.

The reaction may be carried out without isolation of the intermediate formed in step b). By "without isolation" is meant without isolation of the intermediate as a solid. The intermediate may be separated from the reaction mass from which it is formed, but it is not isolated as a solid. Thus, the reaction can proceed without isolation of the intermediate.

Step c): dimethylamination of 2-(4-benzyloxy-phenyl)-acrylic acid alkyl ester with a suitable dimethyl amine source in the presence of a Lewis acid catalyst to form compound A.

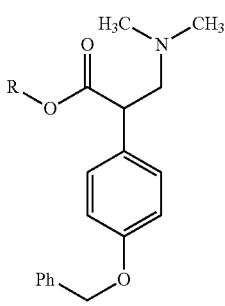

(A)

wherein R is as described above.

The dimethyl amine source used may be selected from dimethyl amine gas and an alcoholic solution of dimethyl amine. A preferred alcohol is methanol.

The Lewis acid catalyst used may be selected from zinc chloride, ferric chloride, aluminium chloride, lithium perchlorate and stannic chloride; preferably selected from ferric chloride and lithium perchlorate.

The dimethylamination may be carried out at a temperature ranging from 0° C. to 50° C., preferably from 25° C. to 30° C.

In a preferred embodiment, steps b) and c) are carried out without isolating the intermediate 2-(4-benzyloxy-phenyl)-acrylic acid alkyl ester.

In another embodiment of the present invention, there is provided a process for the preparation of ODV which process comprises converting compound A to ODV. An embodiment of the process can be schematically represented as shown below in Scheme 3.

SCHEME 3

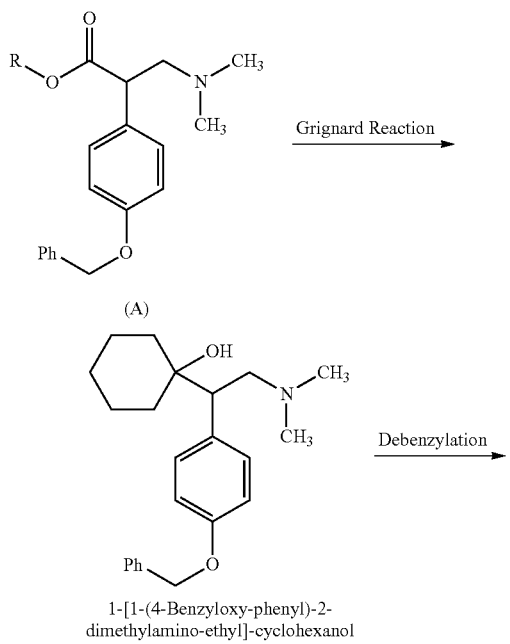

1-[1-(4-Benzyloxy-phenyl)-2-dimethylamino-ethyl]-cyclohexanol

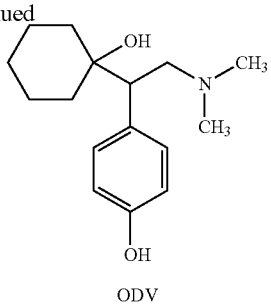

ODV wherein R is as described above.

Accordingly, in an embodiment, the present invention provides a process for the preparation of ODV using compound A comprising steps d) and e), as described below.

Step d): reacting compound A with a Grignard reagent in the presence of a cyclic or acyclic ether as a solvent, to form 1-[1-(4-benzyloxy-phenyl)-2-dimethylamino-ethyl]-cyclohexanol of formula IV.

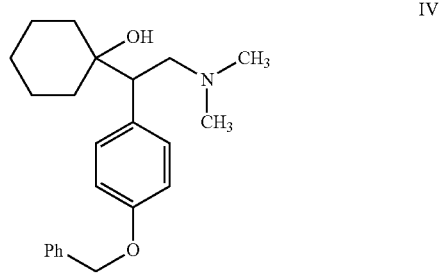 [SMILES: CN(C)CC(c1ccc(OCc2ccccc2)cc1)C1(O)CCCCC1]

IV

The Grignard reagent is typically pentamethylene-1,5-bis(magnesium halide), i.e. XMg—(CH$_2$)$_5$—MgX, where X is halo, for example, chloro, bromo or iodo. The Grignard reagent may be prepared by refluxing activated magnesium turnings and iodine crystals with 1,5-dihalopentane in the presence of cyclic or acyclic ether. The dihalopentane may be selected from dibromopentane, dichloropentane and diiodopentane, preferably dibromopentane.

The cyclic ether that may be used in the process may be selected from ethylene oxide, 1,4-dioxane, furan, dihydrofuran and tetrahydrofuran, anisole, crown ethers; preferably tetrahydrofuran.

The acyclic ether that may be used in the process may be selected from dimethyl ether, methyl tertiary butyl ether and diethyl ether, dimethoxy ethane, dipropyl ether, dibutyl ether, dipentyl ether, methyoxyethane; preferably diethyl ether.

The reaction may be carried out at a temperature ranging from 0° C. to 50° C., preferably from 25° C. to 30° C.

Step e): deprotection of 1-[1-(4-benzyloxy-phenyl)-2-dimethylamino-ethyl]-cyclohexanol to form ODV.

The debenzylation may involve hydrogenation, preferably catalytic hydrogenation with hydrogen gas in the presence of a noble metal catalyst or using a phase transfer hydrogenation, to obtain ODV. Alternatively, other deprotecting reagents may be used, such as mineral acids, strong acids, Lewis acids or aqueous mineral bases in a suitable solvent.

A preferred method for hydrogenation is catalytic reduction with hydrogen gas using a noble metal catalyst selected from palladium, palladium hydroxide, palladium on activated carbon, palladium on alumina, platinum, platinum on activated carbon and Raney nickel.

The solvent used in step (e) may be selected from alkyl acetates, lower alkyl amines, alcohols, aliphatic hydrocarbons, aromatic hydrocarbons, heterocycles, dialkylethers, a mixture of water and water miscible solvents, ionic liquids, halogenated solvents and mixtures thereof.

In this embodiment, the reduction is suitably carried out at a temperature ranging from about 25° C. to about the reflux temperature of the solvent used.

The process of the present invention may further comprise: converting ODV of formula I to a pharmaceutically acceptable salt thereof, by reacting ODV with a suitable acid to form an acid addition salt with the ODV. The acid addition salts include inorganic acids such as hydrochloric acid, hydrobromic acid, sulfuric acid, nitric acid, phosphoric acid, pivalic acid and organic salts such as fumaric acid, tartaric acid, acetic acid, oxalic acid, malonic acid, mandelic acid, succinic acid, maleic acid, lactic acid, citric acid, methane sulfonic acid, p-hydroxy benzoic acid, 1-hydroxy-2-naphthoic acid, glutmic acid, p-toluene sulfonic acid, preferably succinic acid, oxalic acid and 1-hydroxy-2-naphthoic acid.

Various modifications may be made to the embodiments disclosed herein; therefore the above description should not be construed as limiting.

EXAMPLES

The following examples, which include preferred embodiments, will serve to illustrate the practice of this invention, it being understood that the particulars shown are by way of example and for purpose of illustrative discussion of preferred embodiments of the invention.

Example 1

Preparation of (4-benzyloxy-phenyl)-acetic acid methyl ester

Thionyl chloride (60 ml; 0.83 mol) was added drop-wise to a mixture of (4-benzyloxy-phenyl)acetic acid (100 gm; 0.4132 mol) and methanol (300 ml) under constant stirring while maintaining the temperature at 5-10° C. After complete addition, the reaction mixture was stirred for 5-6 hours at room temperature. After completion of the reaction, white crystalline solid was isolated by filtration to yield (4-benzyloxy-phenyl)-acetic acid methyl ester. Yield: 104 g, Efficiency: 98.31%.

Example 2

Preparation of 2-(4-Benzyloxy-phenyl)-acrylic acid methyl ester

Preparation 1
(4-benzyloxy-phenyl)-acetic acid methyl ester (10 g; 0.03906 mol) was charged to toluene (100 ml). Further, potassium carbonate (16.17 g; 0.116 mol), paraformaldehyde (3.51 g, 0.116 mol) and tetrabutyl ammonium bromide (1.25 g) were charged and the reaction mixture thus obtained was refluxed for 5.5-6 hours. The reaction mass was cooled to 25-30° C. and filtered. The filtrate contains 2-(4-benzyloxy-phenyl)-acrylic acid methyl ester.
Preparation 2
(4-benzyloxy-phenyl)-acetic acid methyl ester (10 g; 0.03906 mol) was charged to toluene (100 ml). Further sodium carbonate (12.49 g; 0.12 mol), paraformaldehyde (3.51 g, 0.116 mol) and tetrabutyl ammonium Iodide (1.25 g) were charged and the reaction mixture thus obtained was refluxed for 5.5-6 hours. The reaction mass was cooled to 25-30° C. and filtered. The filtrate contains 2-(4-benzyloxy-phenyl)-acrylic acid methyl ester.
Preparation 3
(4-benzyloxy-phenyl)-acetic acid methyl ester (10 g; 0.04 mol)) was charged to toluene (100 ml). Further potassium carbonate (13.47 g; 0.09 mol), paraformaldehyde (2.9 g, 0.097 mol) and tetrabutyl ammonium iodide (0.72 g) were charged and the reaction mixture thus obtained was refluxed for 5.5-6 hours. The reaction mass was cooled to 25-30° C. and filtered. The filtrate contains 2-(4-benzyloxy-phenyl)-acrylic acid methyl ester.

Example 3 a) Preparation of 2-(4-Benzyloxy-phenyl)-3-dimethylamino-propionic acid methyl ester Preparation 1
The solution of 2-(4-benzyloxy-phenyl)-acrylic acid methyl ester obtained in example 2 was stirred with anhydrous lithium perchlorate (1 g; 0.009 mol). The reaction mixture was cooled to 5-10° C. Dimethyl amine gas was bubbled through the mixture at 5-10° C. for about 30 minutes. The temperature of the reaction mass was raised to 25-30° C. with constant stifling for 2 hours. After completion of the reaction, water (100 ml) was added and the reaction mass was cooled to 10-15° C. The pH of the mixture was adjusted to 2-3 by using conc. HCl. Both the layers were settled and separated out. The aqueous layer was cooled to 5-10° C. and basified with 2N NaOH to pH 8-9. The solid 2-(4-benzyloxy-phenyl)-3-dimethylamino-propionic acid methyl ester thus obtained was filtered, washed with water & dried at 50-55° C. for 7-8 hours. Yield: 6.5 g.
Preparation 2
The solution of 2-(4-benzyloxy-phenyl)-acrylic acid methyl ester obtained in examples 2 was stirred with ferric chloride (1 g; 0.006 mol). The reaction mixture was cooled to 5-10° C. Dimethyl amine gas was bubbled through the mixture at room temperature for about 30 minutes to 1 hour. The temperature of the reaction mass was raised to 25-30° C. with constant stirring for 2 hours. After completion of the reaction, water (100 ml) was added and the reaction mass was cooled to 10-15° C. The pH of the mixture was adjusted to 2-3 by using conc. HCl. Both the layers were settled and separated. The aqueous layer was cooled to 5-10° C. and basified with 2N NaOH to pH 8-9. The solid 2-(4-Benzyloxy-phenyl)-3-dimethylamino-propionic acid methyl ester thus obtained was filtered, washed with water & dried at 50-55° C. for 7-8 hours. Yield: 5.1 g.

The following examples of the 2-(4-benzyloxy-phenyl)-3-dimethylamino-propionic acid alkyl ester of formula A were similarly prepared using the process of Example 3:
b) 2-(4-benzyloxy-phenyl)-3-dimethylamino-propionic acid ethyl ester
c) 2-(4-benzyloxy-phenyl)-3-dimethylamino-propionic acid n-propyl ester
d) 2-(4-benzyloxy-phenyl)-3-dimethylamino-propionic acid isopropyl ester
e) 2-(4-benzyloxy-phenyl)-3-dimethylamino-propionic acid n-butyl ester
f) 2-(4-benzyloxy-phenyl)-3-dimethylamino-propionic acid sec-butyl ester
g) 2-(4-benzyloxy-phenyl)-3-dimethylamino-propionic acid tert-butyl ester h) 2-(4-benzyloxy-phenyl)-3-dimethylamino-propionic acid n-pentyl ester
i) 2-(4-benzyloxy-phenyl)-3-dimethylamino-propionic acid neopentyl ester
j) 2-(4-benzyloxy-phenyl)-3-dimethylamino-propionic acid n-hexyl ester Example 4

Preparation of 1-[1-(4-Benzyloxy-phenyl)-2-dimethylamino-ethyl]-cyclohexanol

Preparation 1

Activated magnesium turnings (8 g) and a few crystals of iodine were charged to tetrahydrofuran (200 ml; 2.47 mol). 1,5-dibromopentane (20.7 ml; 0.15 mol) was added to the above mixture, and was refluxed for 2 hours. The reaction mass was cooled to 0-5° C. A solution of 2-(4-benzyloxyphenyl)-3-dimethylamino-propionic acid methyl ester (10 g; 0.032 mol) in tetrahydrofuran (100 ml) was added to the above reaction mass very slowly. The temperature was raised to 25-30° C. with constant stirring for 2 hours. After completion of the reaction; the reaction mass was quenched with saturated ammonium chloride solution (100 ml). The aqueous layer was extracted with ethyl acetate (2×50 ml) and the combined organic layer was washed with water (100 ml). The organic layer was dried on sodium sulphate, concentrated under reduced pressure and the product was isolated in n-heptane (25-30 ml). The material was dried under vacuum at 45-50° C. Yield: 7.0 g, Efficiency: 62%.

Preparation 2

Activated magnesium turnings (8 g) and a few crystals of iodine were charged to methyl t-butyl ether (200 ml; 1.68 mol). After addition of 1,5-dibromopentane (20.7 ml; 0.15 mol), the reaction mixture was refluxed for 2 hours. The reaction mass was cooled to 0-5° C. A solution of 2-(4-benzyloxy-phenyl)-3-dimethylamino-propionic acid methyl ester (10 g; 0.032 mol) in methyl t-butyl ether (100 ml) was added to the above reaction mass very slowly. The temperature was raised to 25-30° C. with constant stirring for 2 hours. After completion of the reaction, reaction mass was quenched with saturated ammonium chloride solution (100 ml). The aqueous layer was extracted with ethyl acetate (2×50 ml) and the combined organic layer was washed with water (100 ml). The organic layer was dried on sodium sulphate, concentrated under reduced pressure and the product was isolated in n-heptane (25-30 ml). The material was dried under vacuum at 45-50° C. Yield: 5.9 g, Efficiency: 52.35%.

Preparation 3

Activated magnesium turnings (8 g) and a few crystals of iodine were charged to diethyl ether (200 ml). After addition of 1,5-dibromopentane (20.7 ml; 0.15 mol), the reaction mixture was refluxed for 2 hours. The reaction mass was cooled to 0-5° C. Separately prepared solution of 2-(4-benzyloxy-phenyl)-3-dimethylamino-propionic acid methyl ester (10 g; 0.032 mol) in diethyl ether (100 ml) was added to the above reaction mass very slowly. The temperature was raised to 25-30° C. with constant stirring for 2 hours. After completion of the reaction; the reaction mass was quenched with saturated ammonium chloride solution (100 ml). The aqueous layer was extracted with ethyl acetate (2×50 ml) and the combined organic layer was washed with water (100 ml). The organic layer was dried on sodium sulphate, concentrated under reduced pressure and the product was isolated in n-heptane (25-30 ml). The material was dried under vacuum at 45-50° C. Yield: 7 g, Efficiency: 62%.

Example 5

Preparation of ODV

1-[1-(4-benzyloxy-phenyl)-2-dimethylamino-ethyl]-cyclohexanol (2 gm; 0.006 mol) was debenzylated in the presence of hydrogen gas over 10% Pd/C (0.4 gm) in specially purified denatures spirit (SPDS)-toluene (50 ml) under 150 psi pressure and at 25° C. for about 4.0 hours. After completion of the reaction, catalyst was removed by filtration, the filtrate was concentrated to obtain residue. Ethyl acetate (10 ml) was added to the residue, stirred for 30 minutes at 50° C. and further stirred for 30 min to 1 hour at room temperature. The solid was isolated by filtration to obtain ODV (1.3 g, 0.005 mol) as an off-white crystalline solid. Efficiency: 87.24%.

Example 6

Preparation of ODV Succinate

O-desmethyl venlafaxine (10 gm; 0.038 mol) was stirred with acetone:water (3.5:1) mixture (90 ml). To the reaction mass, succinic acid (5.38 gm; 0.029 mol) was added. The mixture was heated to 60-65° C. for 30 minutes. Activated charcoal (1 gm) was added to the reaction mixture and heated to reflux for 30 minutes. The mixture was filtered through hyflo bed and washed with acetone (10 ml). The filtrate was cooled gradually to room temperature and further chilled to 0-5° C. The solid obtained was isolated by filtration and washed with chilled acetone to obtain ODV succinate.

The salt was further purified by dissolving in acetone:water (3.5:1) mixture (84 ml). The solution was heated to 60-65° C. for 1 hour. The mixture was cooled gradually to room temperature and further chilled to 0-5° C. for 30 minutes. The solid was isolated by filtration and further dried in a vacuum oven at 45-50° C. Yield: 11.7 gm, Efficiency: 80.68%.

Example 7

Preparation of ODV Oxalate

O-desmethyl venlafaxine (10 gm; 0.038 mol) was stirred with acetone:water (3.5:1) mixture (90 ml). To the reaction mass, oxalic acid (5.8 gm; 0.046 mol) was added. The mixture was heated to 60-65° C. for 30 minutes. Activated charcoal (1 gm) was added to the reaction mixture and heated to reflux for 30 minutes. The mixture was filtered through hyflo bed and washed with acetone (10 ml). The filtrate was cooled gradually to room temperature and further chilled to 0-5° C. The solid obtained was isolated by filtration and washed with chilled acetone to obtain ODV oxalate.

The salt was further purified by dissolving in acetone:water (3.5:1) mixture (84 ml). The mixture was heated to 60-65° for 1 hour. The mixture was cooled gradually to room temperature and further chilled to 0-5° C. for 30 minutes. The solid was isolated by filtration and further dried in a vacuum oven at 45-50° C. Yield: 9.8 gm, Efficiency: 73.13%.

Example 8

Preparation of ODV 1-hydroxy-2-naphthoate

O-desmethyl venlafaxine (10 gm; 0.038 mol) was stirred with acetone:water (3.5:1) mixture (90 ml). To the reaction mass, 1-hydroxy-2-naphthoic acid (8.14 gm; 0.043 mol) was added. The mixture was heated to 60-65° C. for 30 minutes. Activated charcoal (1 gm) was added to the reaction mixture and heated to reflux for 30 minutes. The mixture was filtered through hyflo bed and washed with acetone (10 ml). The filtrate was cooled gradually to room temperature and further chilled to 0-5° C. The solid obtained was isolated by filtration and washed with chilled acetone to obtain ODV 1-hydroxy-2-naphthoate.

The salt obtained was purified by dissolving in acetone: water (3.5:1) mixture (84 ml). The mixture was heated to 60-65° for 1 hour. The mixture was cooled gradually to room temperature and further chilled to 0-5° C. for 30 minutes. The solid was isolated by filtration and further dried in a vacuum oven at 45-50° C. Yield: 10.3 gm; Efficiency: 60.23%.

It will be appreciated that the invention may be modified within the scope of the appended claims.

The invention claimed is:

1. A process for preparing O-desmethyl venlafaxine (ODV) of formula V

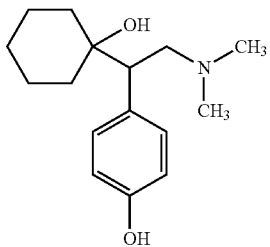

V comprising converting a compound of formula A

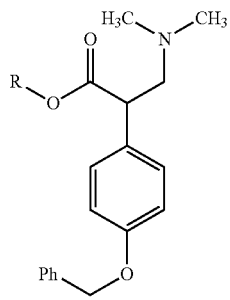

(A)

to ODV, wherein R is an alkyl group, wherein converting the compound of Formula A to ODV comprises:
  d) reacting compound A with a Grignard reagent in the presence of a cyclic or acyclic ether as a solvent to form 1-[1-(4-benzyloxy-phenyl)-2-dimethylamino-ethyl]-cyclohexanol of formula IV;

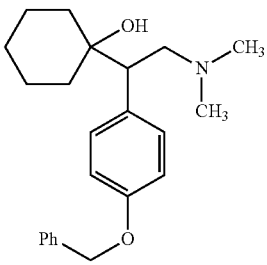

IV and
  e) deprotecting 1-[1-(4-benzyloxy-phenyl)-2-dimethylamino-ethyl]-cyclohexanol to form ODV.

2. The process according to claim 1, wherein the compound A has been prepared according to a process comprising: a) esterifying (4-benzyloxy-phenyl)acetic acid of formula I

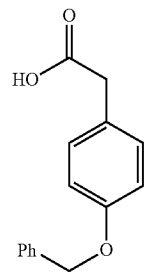

I to form a (4-benzyloxy-phenyl)-acetic acid alkyl ester of formula II;

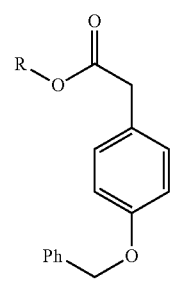

II b) reacting the (4-benzyloxy-phenyl)-acetic acid alkyl ester of Formula II with a paraformaldehyde in the presence of an inorganic base and a phase transfer catalyst to form a 2-(4-benzyloxy-phenyl)-acrylic acid alkyl ester of Formula II

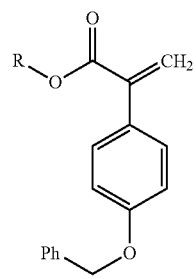

III

; and
  c) reacting the 2-(4-benzyloxy-phenyl)-acrylic acid alkyl ester of formula III with dimethylamine in the presence of a Lewis acid catalyst to form the compound of formula A.

3. The process according to claim 1, wherein the Grignard reagent is $XMg-(CH_2)_5-MgX$, where X is halo.

4. The process according to claim 1, wherein the Grignard reagent is prepared by refluxing activated magnesium turnings and iodine crystals with 1,5-dihalopentane in the presence of a cyclic or acyclic ether.

5. The process according to claim 4, wherein the dihalopentane is selected from dibromopentane, dichloropentane and diiodopentane, preferably dibromopentane.

6. The process according to claim 1, wherein the solvent is a cyclic ether selected from the ethylene oxide, 1,4-dioxane, furan, dihydrofuran, tetrahydrofuran, anisole and a crown ether; preferably tetrahydrofuran.

7. The process according to claim 1, wherein the solvent is an acyclic ether selected from dimethyl ether, methyl tertiary butyl ether, diethyl ether, dimethoxy ethane, dipropyl ether, dibutyl ether, dipentyl ether and methoxyethane; preferably diethyl ether.

8. The process according to claim 1, wherein the debenzylation in step e) comprises hydrogenation, preferably catalytic hydrogenation with hydrogen gas in the presence of a noble metal catalyst or using a phase transfer hydrogenation, to obtain ODV.

9. The process according to claim 8, wherein the noble metal catalyst is selected from palladium, palladium hydroxide, palladium on activated carbon, palladium on alumina, platinum, platinum on activated carbon and Raney nickel.

10. The process according to claim 8, wherein the hydrogenation is carried out in a solvent selected from an alkyl acetate, a lower alkyl amine, an alcohol, an aliphatic hydrocarbon, an aromatic hydrocarbon, a heterocycle, a dialkylether, a mixture of water and a water miscible solvent, an ionic liquid, a halogenated solvent and mixtures thereof.

11. The process according to claim 1, wherein the ODV is converted to a pharmaceutically acceptable acid addition salt thereof.

12. The process according to claim 11, wherein the pharmaceutically acceptable acid is selected from hydrochloric acid, hydrobromic acid, sulfuric acid, nitric acid, phosphoric acid, pivalic acid, fumaric acid, tartaric acid, acetic acid, oxalic acid, malonic acid, mandelic acid, succinic acid, maleic acid, lactic acid, citric acid, methane sulfonic acid, p-hydroxy benzoic acid, 1-hydroxy-2-naphthoic acid, glutamic acid and p-toluene sulfonic acid.

13. The process according to claim 12, wherein the acid is succinic acid, oxalic acid or 1-hydroxy-2-naphthoic acid.

14. The process according to claim 1, wherein R is a C1-C10 alkyl group.

15. The process according to claim 1, wherein R is methyl or ethyl.

16. The process according to claim 1, further comprising:
a) esterifying (4-benzyloxy-phenyl)-acetic acid of formula I

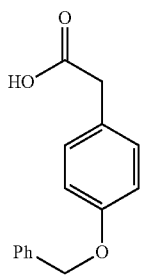

to form a (4-benzyloxy-phenyl)-acetic acid alkyl ester of formula II;

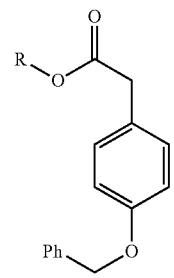

b) reacting the (4-benzyloxy-phenyl)-acetic acid alkyl ester of formula II with paraformaldehyde in the presence of an inorganic base and a phase transfer catalyst to form a 2-(4-benzyloxy-phenyl)-acrylic acid alkyl ester of formula III; and

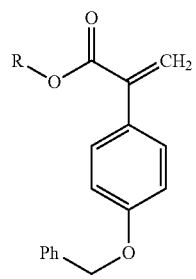

c) reacting the 2-(4-benzyloxy-phenyl)-acrylic acid alkyl ester of formula III with dimethylamine in the presence of a Lewis acid catalyst to form the compound of formula A.

17. The process according to claim 16, wherein R is a C1-C10 alkyl group.

18. The process according to claim 16, wherein R is methyl or ethyl.

19. The process according to claim 16, wherein esterification comprises reacting the acid of formula I with an alcoholic acid solution.

20. The process according to claim 16, wherein esterification comprises reacting (4-benzyloxy-phenyl)-acetic acid with a mixture of an alcohol and thionyl chloride or potassium carbonate and dimethyl sulfate.

21. The process according to claim 20, wherein the alcohol is methanol.

22. The process according to claim 16, wherein the inorganic base used in step b) is selected from: an alkali metal hydroxide, preferably sodium hydroxide or potassium hydroxide; and an alkali metal carbonate, preferably potassium carbonate, sodium carbonate or cesium carbonate.

23. The process according to claim 22, wherein the inorganic base is an alkali metal carbonate, preferably potassium carbonate.

24. The process according to claim 16, wherein the phase transfer catalyst in step b) is selected from; tetrabutyl ammonium hydrogen sulfate; an ammonium halide, preferably triethyl benzyl ammonium chloride; an alkyl ammonium halide, preferably tetrabutyl ammonium bromide or tetrabutyl ammonium iodide, most preferably tetrabutyl ammonium iodide.

25. The process according to claim 16, wherein step b) is carried out in the presence of an organic solvent selected from toluene, chlorobenzene and o-xylene; preferably toluene.

26. The process according to claim 16, wherein the source of dimethyl amine in step c) is dimethyl amine gas Or an alcoholic solution of dimethyl amine.

27. The process according to claim 26, wherein the alcohol is methanol.

28. The process according to claim 16, wherein the Lewis acid catalyst used in step c) is selected from zinc chloride, ferric chloride, aluminium chloride, lithium perchlorate and stannic chloride; preferably from ferric chloride and lithium perchlorate.

29. The process according to claim 16, wherein steps b) and c) are carried out without isolation of the 2-(4-benzyloxy-phenyl)-acrylic acid alkyl ester of formula III

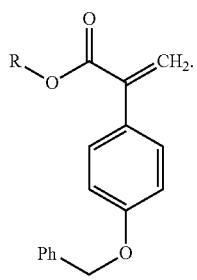

* * * * *

UNITED STATES PATENT AND TRADEMARK OFFICE
CERTIFICATE OF CORRECTION

PATENT NO. : 9,012,689 B2
APPLICATION NO. : 13/381870
DATED : April 21, 2015
INVENTOR(S) : Rajendra Narayanrao Kankan, Dharmaraj Ramachandra Rao and Manohar Raghunath Surve It is certified that error appears in the above-identified patent and that said Letters Patent is hereby corrected as shown below:

In the claims:

Claim 2, Column 16, Line 38, replace "with a paraformaldehyde" with --with paraformaldehyde--.

Claim 2, Column 16, Line 40, replace "of Formula II" with --of Formula III--.

Claim 26, Column 19, Line 2, replace "gas Or an" with --gas or an--.

Signed and Sealed this
Eighth Day of September, 2015

Michelle K. Lee
*Director of the United States Patent and Trademark Office*